United States Patent
Wade

(10) Patent No.: US 6,273,716 B1
(45) Date of Patent: *Aug. 14, 2001

(54) PROPHYLACTIC COVERS FOR DENTAL INSTRUMENTS AND METHODS FOR MAKING THE SAME

(76) Inventor: Eric Wade, 11335 Scenic Dr., Tyler, Smith County, TX (US) 75209

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,584

(22) Filed: Oct. 22, 1999

(51) Int. Cl.[7] .................................................. A61C 1/16
(52) U.S. Cl. ............................................................ 433/116
(58) Field of Search ...................................... 433/116, 115

(56) References Cited

U.S. PATENT DOCUMENTS

| 949,273 | * | 2/1910 | Hinrichsen | 433/116 |
|---|---|---|---|---|
| 1,497,561 | * | 6/1924 | Gruss | 433/116 |
| 4,050,894 | | 9/1977 | Genis | 21/86 |
| 4,182,041 | | 1/1980 | Girard | 433/115 |
| 4,286,950 | | 9/1981 | Hawk | 433/116 |
| 4,615,679 | | 10/1986 | Wyatt | 433/229 |
| 4,693,871 | | 9/1987 | Geller | 433/116 |
| 4,728,290 | | 3/1988 | Eisner et al. | 433/116 |
| 4,776,791 | | 10/1988 | Hannula | 433/4 |
| 4,789,336 | | 12/1988 | Lewis | 433/116 |
| 4,810,194 | | 3/1989 | Snedden | 433/91 |
| 4,998,880 | | 3/1991 | Nerli | 433/80 |
| 5,267,861 | | 12/1993 | Daemer | 433/116 |
| 5,407,354 | | 4/1995 | Fife | 433/116 |
| 5,466,561 | | 11/1995 | Rantanen | 430/347 |
| 5,480,302 | | 1/1996 | Fife | 433/116 |
| 5,490,781 | | 2/1996 | Wade | 433/116 |
| 5,807,107 | | 9/1998 | Bright | 433/116 |

* cited by examiner

Primary Examiner—Nicholas D. Lucchesi
(74) Attorney, Agent, or Firm—James J. Murphy, Esq.; Winstead Sechrest & Minick

(57) ABSTRACT

A cover 30 for a selected dental hand piece 10 includes a body 32 having first and second halves 34a, 34b of a shape and dimensions selected to substantially conform with a shape and dimensions of selected hand piece 10, said halves. Hinge 36 couples the first and second halves 34a, 34b of body 32 for allowing the first half 34a to rotate with respect to the second half 34b to thereby form an enclosure for enclosing a substantial portion of hand piece 10. The enclosure includes a head portion 42, handle portion 32 and a substantially rigid neck portion 40 between handle portion 32 and head portion 42.

23 Claims, 3 Drawing Sheets

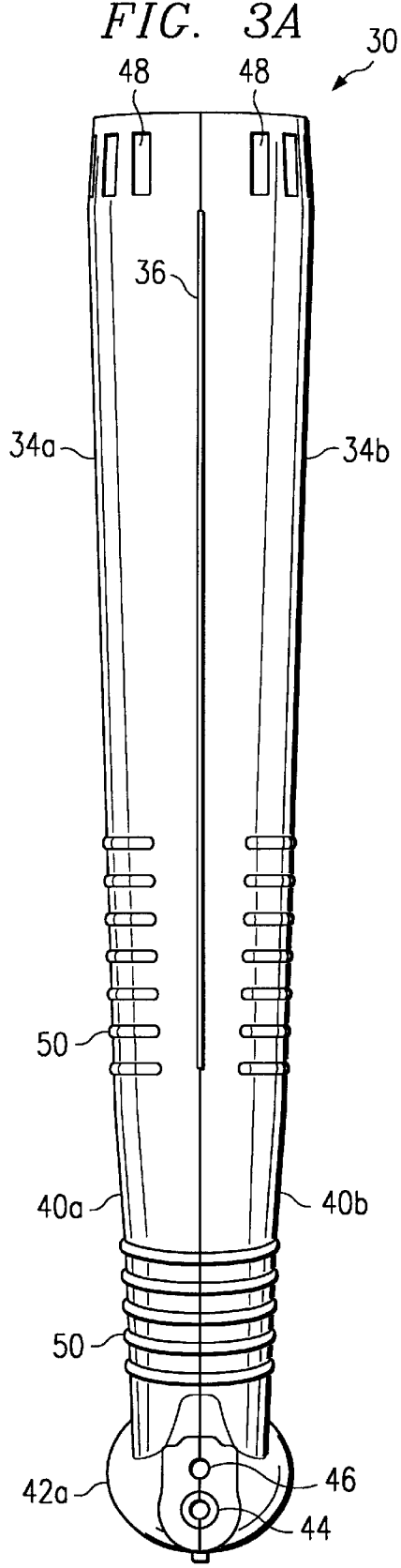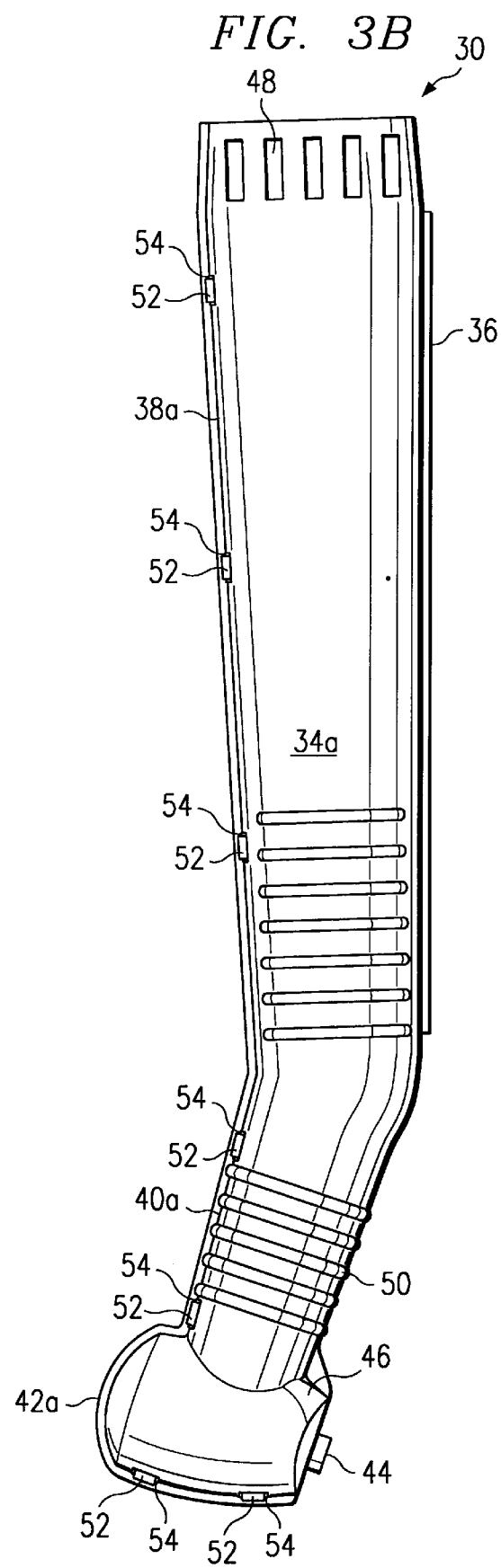

PROPHYLACTIC COVERS FOR DENTAL INSTRUMENTS AND METHODS FOR MAKING THE SAME

BACKGROUND OF THE INVENTION

1. Field of the Invention

The present invention relates in general to dental instruments and in particular to prophylactic covers for dental instruments and methods for making the same.

2. Description of the Related Art

In recent years, the various health professions have come under close scrutiny due to the increased possibility of the transmission of infectious diseases from doctor to patient, patient to doctor, and patient to patient. This is particularly true in the dental office, where dental appliances come in direct contact with potentially harmful fluids or blood-born pathogens, such as Hepatitis B and HIV, found within the oral cavity. With the predicted increase in the number of cases of infection with the Hepatitis B and HIV viruses, dentists will be treating more patients carrying these infections, knowingly or unknowingly. Consequently, the possibility of accidental transmission of these dangerous infectious diseases will correspondingly increase.

One particular path of pathogen transmission within the dental office is through the high speed and low speed air-driven dental hand pieces. These appliances come in direct contact with the patient's oral cavity during use and often collect blood, minute debris and other microbial and particulate matter, which have been shown to be a source of blood-born pathogen transmission, including the transmission of the Hepatitis B and HIV viruses. Because of the potential for transmission of pathogens by dental hand pieces, the Occupational Safety and Health Administration has issued detailed guidelines for proper handling and sterilization of these devices following each patient use. Among other things, proper hand piece sterilization involves autoclaving the instrument at approximately 15 psi and 121° C. for a period of thirty minutes (cold sterilization using a disinfectant solution is often ineffective). This requirement, although necessary, drastically reduces the number of patients that can be effectively treated during the dentist's normal work day due to the increased time required to both autoclave and cool instruments. (The cost of dental hand pieces range from a few hundred to well over a thousand dollars, which makes it economically difficult to maintain a large number of such appliances in order to handle an increased patient load). Moreover, repetitive autoclaving has been shown to decrease the useful life of the instruments themselves.

Another concern related to the use of high-speed dental hand pieces is the noise level at which the dentist is exposed. The typical high-speed dental hand piece produces noise in the frequency range of 2,000 to 3,500 Hertz, with a typical amplitude of 80 decibels at approximately 2,000 Hertz. With the average dentist spending many hours per week, over a number of years, exposed to the noise from dental appliances, the potential readily exists for the dental practitioner to experience some type of hearing disorder.

In sum, the need has arisen for apparatus and methods which provide a practical means for preventing dental hand pieces from coming in direct contact with potentially harmful fluids or blood-born pathogens found within the oral cavity. Moreover, it would be highly advantageous if such methods and apparatus could also reduce the noise level to which the dental practitioner is exposed during the use of such hand pieces.

SUMMARY OF THE INVENTION

The principles of the present invention are embodied in a cover for a selected dental hand piece. The body includes first and second halves of a shape and dimensions selected to substantially conform with a shape and dimensions of the selected hand piece. The halves are mirror symmetric. Means are also provided for coupling the first and second halves of the body and allowing the first half to rotate with respect to the second half to thereby form an enclosure for enclosing a substantial portion of the hand piece. The enclosure includes a head portion, handle portion and a substantially rigid neck portion between handle portion and head portion, each corresponding to a portion of the hand piece.

The inventive principles are also embodied in a prophylactic device for minimizing exposure of selected portions of a dental hand piece to potentially contaminated matter. The device includes a body formed of a layer of substantially rigid material including integral handle, neck and head portions each having a shape and dimensions preselected to substantially conform with the corresponding handle, neck and head portions of the hand piece. The body comprises first and second halves, symmetric along a longitudinal axis of the body. An integral hinge is included for rotating the first half of the body for engagement with the second half, a first sidewall of the body defining an enclosures for encompassing the handle, neck and head portions of the hand piece.

The invention can also be embodied in a dental appliance including a dental hand piece and a protective cover enclosing the hand piece. The protective cover includes a body substantially conforming in shape and dimensions with the hand piece and having first and second halves symmetric along a longitudinal axis of the body. The cover further includes integral means for rotating the first half of the body for engagement with the second half, thereby defining an enclosure adapted to enclose the hand piece. Integral means retain the first and second halves in engagement and enclosure of the hand piece.

A method of constructing a protective cover for a dental hand piece is also disclosed. A mold is constructed having a shape and dimensions corresponding to a selected model of dental hand piece and defining symmetric halves of head, neck and handle portions of the cover along with hinge means for folding the halves into engagement. The cover is then formed from the selected plastic using the mold.

The principles of the present invention provide substantial advantages over the prior art. Among other things, both halves of the protective cover can be formed and distributed as a single unitary body. Moreover, according to these principles, each cover is specifically designed to conform with the dimensions and shape of various available dental hand pieces. Moreover, ribs are provided on the inner surface of the hand piece to isolate the hand piece from the cover and thereby reduce the noise experienced by the dental practitioner.

BRIEF DESCRIPTION OF THE DRAWINGS

For a more complete understanding of the present invention, and the advantages thereof, reference is now made to the following descriptions taken in conjunction with the accompanying drawings, in which:

FIGS. 3A and 3B are diagrams depicting respective side views of the disposable cover of FIG. 2 in the closed or folded configuration.

DESCRIPTION OF THE PREFERRED EMBODIMENTS

Figure 1:
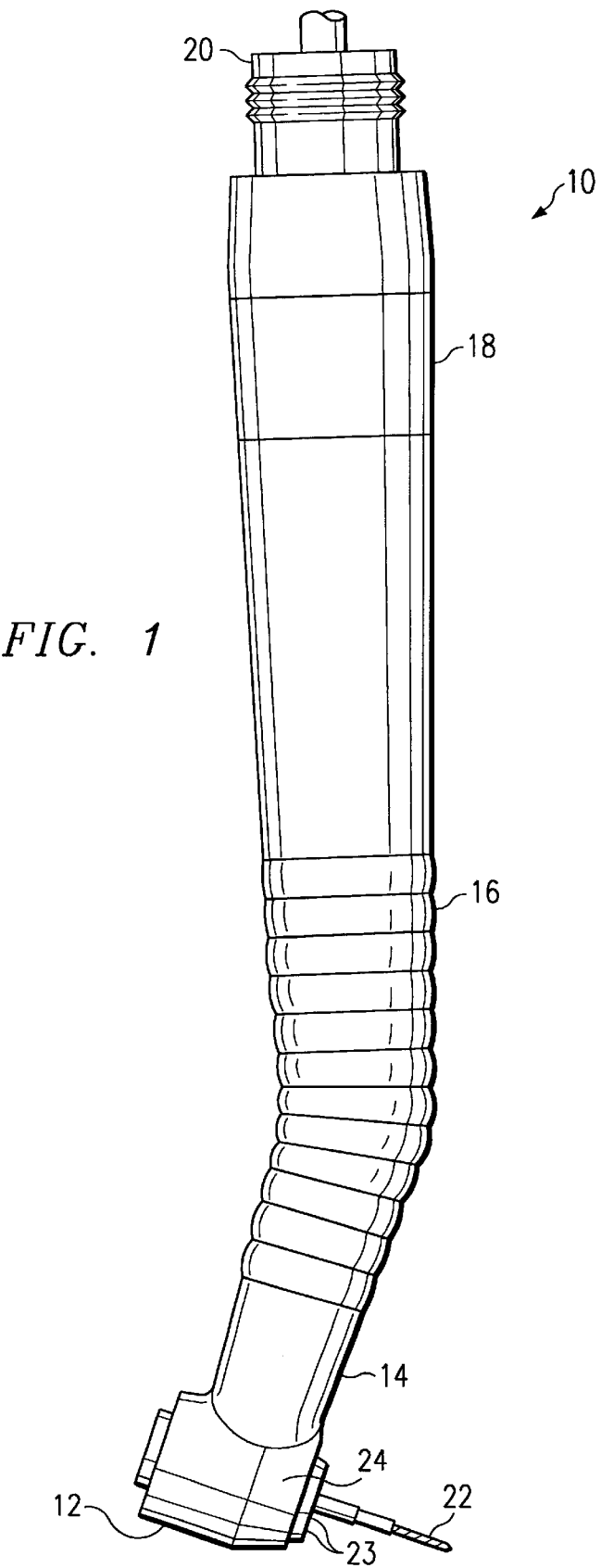
FIG. 1 is a diagram of an exemplary high-speed air driven dental hand piece which includes a head, neck, and body.
Figure 2:
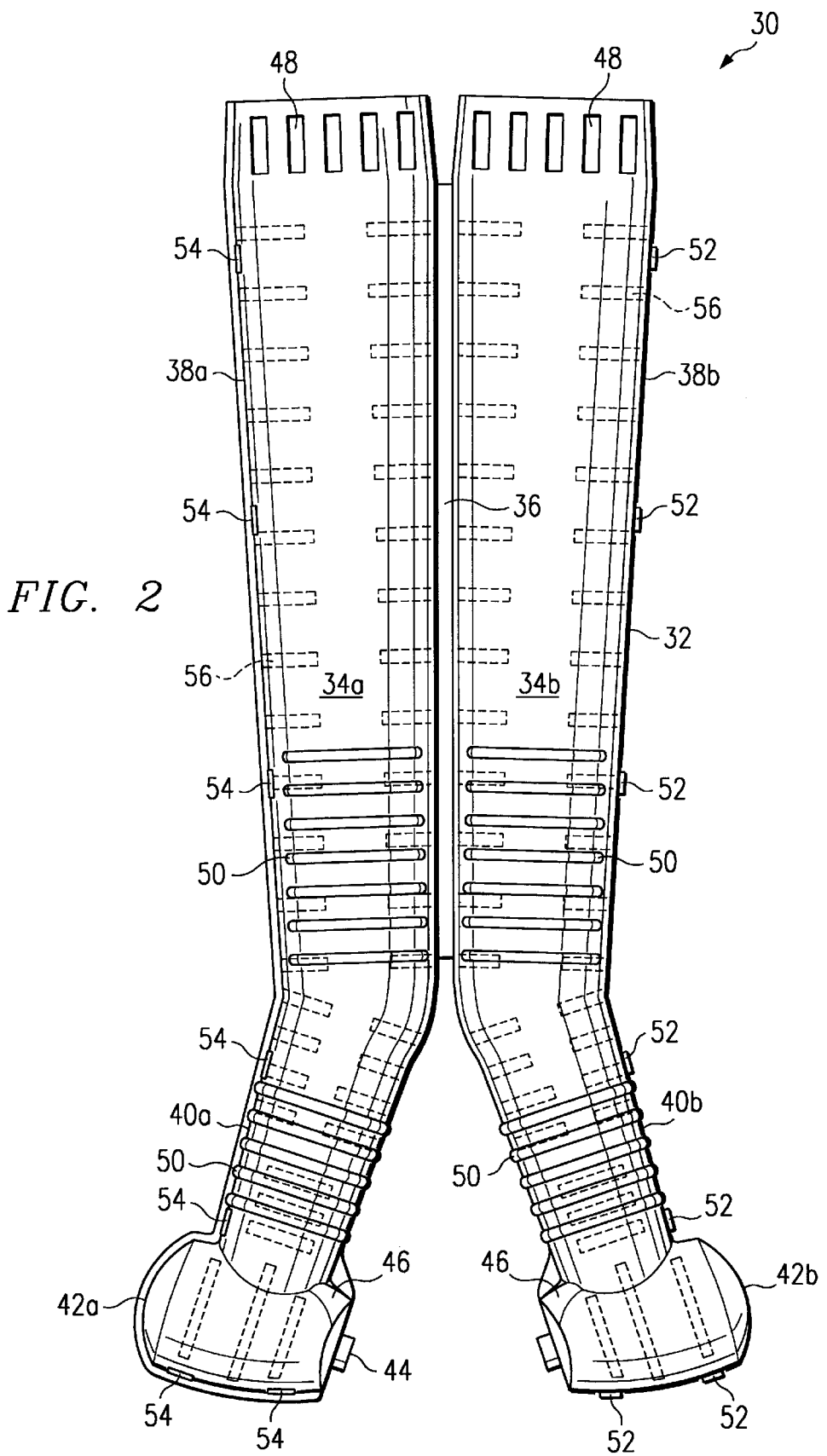
FIG. 2 is a diagram depicting a disposable cover in the open or unfolded configuration.

The principles of the present invention and their advantages are best understood by referring to the illustrated embodiment depicted in FIGS. 1–2 of the drawings, in which like numbers designate like parts.

FIG. 1 is a diagram of an exemplary high-speed air driven dental hand piece 10 which includes a head 12, neck 14, and body 16. In the illustrated embodiment, neck 14 is disposed at a contra-angle to body 16. Body 16 includes a general handle region 18 which facilitates manual manipulation of hand piece 10. Grooves or ribs may be provided along body 16 for improved gripping.

Head 12, neck 14 and body 16 enclose specialized tubing, known in the art, through which both water and pressurized air flow. Specifically, air and water connecting hoses (not shown) couple to a receiving receptacle or connector 20 of hand piece 10 and provide water and pressurized air through hand piece 10. The water and air flow from receptacle 20 through the specialized tubing enclosed within head 12, neck 14 and body 16 of hand piece 10 and exit through air-water openings 22. The pressurized air drives a turbine enclosed within head 12 which in turn drives an interchangeable dental burr 23. Head 12 also includes a burr changing mechanism which includes a socket-like opening 24 through the rear of head 12 which is used to receive a burr tool for a loosening and tightening the burr.

As can be seen from FIG. 1, there are several areas of hand piece 10 which can be contaminated with potentially harmful blood-born pathogens, other micro/viral spores, or debris during normal use in the dental office setting. Of particular concern are the air-water openings 22, the many grooved areas of head 12, neck 14, body 16, including handle region 18, along with the connector hose couplings at receptacle 20. Many of these areas are not easily cleaned or easily reached by chemical disinfectants. Moreover some studies have shown that the air-water spray openings 22 can provide a portal for the entry of potentially contaminated material.

FIG. 2 is a diagram depicting a disposable cover 30 adapted to receive and enclose a dental hand piece, such as a hand piece 10. FIGS. 3A and 3B are respective side views of cover 30 in the closed or folded configuration. In this view, cover 30 is in the open or unfolded configuration.

According to the principles of the present invention, cover 30 is constructed to conform with a specific model hand piece of a given manufacture. This can be done for example by constructing a mold conforming to the size and shape of the selected hand piece and then forming cover 30 by injection molding or thermo-forming using plastic. Assume for discussion purposes that hand piece 10 is a Midwest Quiet-Air Fiber Optic II hand piece available from Midwest American (Dental) Co. In this case, the mold will be constructed such that the shape and dimensions of cover 25 will generally conform to this particular hand piece in accordance with the principles described below.

Cover 30 is preferably formed as a unitary plastic body 32 having two substantially rigid halves 34a and 34b are generally mirror symmetric and are coupled by a thin, integral flexible strip 36. Flexible strip 36 forms a hinge allowing the two halves 34 of body 32 to fold around and enclose the corresponding dental hand piece.

For a further discussion of dental hand pieces and the problems related to their sterilization and use, please refer to coassigned U.S. Pat. No. 5,490,781 issued on Feb. 13, 1996 to Wade for an ADJUSTABLE, SANITARY, NON-REUSABLE HIGH SPEED AND LOW SPEED DENTAL HAND PIECE GLOVE (COVER) AND NOISE REDUCER, incorporated herein by reference.

The two halves of body 32 when folded around thin strip 36, define an elongated handle 38 conforming to the handle portion of the corresponding hand piece. A neck 40, formed at an angle to handle portion 38 corresponds to and encloses the neck portion of the handle piece. Similarly, the two halves of body 32 define a head portion 42 which conforms to and encloses the head of the corresponding dental hand piece.

In the illustrated embodiment, head portion 42 includes aperture 44, which may be collared, through which the hand piece burr extends. Additionally, a second aperture 46 is shown through which water and air are ejected. In alternate embodiments, the head portion may have a different aperture configuration, depending on the model hand piece. For example, alternate embodiments may include an aperture for a fibre optic light. Each half 38 of the handle portion includes a series of apertures or slits 48 through which the pressurized air exhaust from the hand piece turbine vents. These vents prevent the turbine from stalling due to backpressure from its own exhaust. The outer surface of body 32 further includes a number of spaced-apart ribs or protrusions 50 for facilitating gripping of the cover/hand piece assembly during use.

When cover 30 is in use, and enclosing the corresponding hand piece, the two halves 34a and 34b are held together by a series of connectors preferable consisting of a series of male connectors or protrusions periodically disposed along the outer edge of half-body 34a and corresponding set of female apertures 54 disposed along the edge of half-body 34b. Male connectors 52 include a notch which when inserted through female receptacles 54, latch on the side wall of body 32 thereby holding the outer edges of half body portions 34 together such that cover 30 encloses the corresponding dental headpiece.

Along the opposite surface of each half 34, are formed a series of spaced apart ribs or protrusions 56. In the closed configuration of FIGS. 3A and 3B, ribs 56 are disposed along the inner surface or sidewall of cover 30. Ribs 56 contact the enclosed hand piece and isolate it from the side walls of body 32. Moreover, ribs 58 form a series of baffles along the length of body 32. This provides the substantial advantage of reducing the noise and vibration experienced by the dental practitioner handling the hand piece/cover assembly.

In the preferred embodiment, cover 30 is provided in a protective, aseptic package in the open configuration of FIG. 2. When needed, cover 30 is removed from its packaging and the sterilized hand piece placed within the conforming side walls of one half 34 of body 32. Once the hand piece is properly centered, the other half of 34 of body 32 is rotated around hinge 36 such that the male latches 52 engage the female receptacles 54. The complete assembly comprising the hand piece and cover 32 are now ready for use in the desired dental procedure.

During the procedure, water and air are forced through air-water aperture 46 to the operating field in the oral cavity. Exhaust air from the turbine spinning the burr is also forced out of cover 30 through venting apertures 48. In the closed configuration, protective cover 30 isolates the hand tool from saliva, blood or other potentially harmful debris produced during the procedure. Then, when the procedure is complete, gentle force is applied until the interlocking mechanism provided by latches 52 and apertures 54 is broken. The used cover 30 can then be simply discarded similar to other potentially hazardous biomedical waste.

Although the invention has been described with reference to a specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed:

1. A cover for a selected dental hand piece comprising:
   a single-piece body having first and second halves of a shape and dimensions selected to substantially conform with a shape and dimensions of said selected hand piece, said halves being mirror symmetric;
   hinge means forming a part of said single-piece body and coupling said first and second halves of said body for allowing said first half to rotate with respect to said second half to thereby form an enclosure for enclosing a substantial portion of said hand piece, said enclosure including a head portion, a handle portion and a substantially rigid neck portion between said handle portion and said head portion; and
   means for engaging said first half with said second half to maintain said enclosure about said hand piece.

2. The cover of claim 1 wherein said head portion and said handle portion are substantially rigid.

3. The cover of claim 1 wherein said means for engaging comprises an aperture formed through an edge portion of said first half of said body and a reciprocal latch formed through at an edge portion of said second half of said body.

4. The cover of claim 1 and wherein said body comprises an inner wall and further comprises a plurality of spaced apart protrusions extending from said inner wall into a space defined by said enclosure for contacting said hand piece.

5. The cover of claim 1 wherein said body is formed of a substantially rigid plastic.

6. A prophylactic device for minimizing exposure of selected portions of a dental hand piece to potentially contaminated matter comprising:
   a single-piece body formed of a layer of substantially rigid material including an integral handle, neck and head portions each having a shape and dimensions preselected to substantially conform with corresponding handle, neck and head portions of said hand piece, said body comprising first and second halves symmetric along a longitudinal axis of said body; and
   a hinge forming a part of said single-piece body for rotating said first half of said body for engagement with said second half, a first sidewall of said body defining an enclosure for encompassing said handle, neck and head portions of said hand piece.

7. The prophylactic device claim 6 and further comprising a plurality of protrusions extending into said enclosure from selected points on said first sidewall of said body for spacing said first sidewall and said hand piece.

8. The prophylactic device of claim 7 wherein said protrusions comprise a plurality of ribs.

9. The prophylactic device of claim 7 wherein said body is formed of a substantially rigid plastic.

10. The prophylactic device of claim 7 and further comprising a plurality of protrusions extending from a second sidewall of said body for facilitating manual gripping, said second sidewall defined by a surface of said layer opposing a surface defining said first sidewall.

11. The prophylactic device of claim 7 wherein said head portion includes an aperture through said layer for receiving a bur.

12. The prophylactic device of claim 11 wherein said head portion further includes an aperature through said layer for expelling water received through a receptacle through a distal end of said body.

13. The prophylactic device of claim 11 wherein said head portion further includes an aperture through said layer for receiving a fibre optic light.

14. The prophylactic device of claim 6 and further comprising means for maintaining said first and second halves in engagement.

15. The prophylactic device of claim 14 wherein said means for maintaining said first and second halves in engagement comprises a plurality of latches formed at selected points along an edge of said first half of said body and opposing apertures formed along an edge of said second half of said body.

16. A dental appliance comprising:
    a dental hand piece; and
    a protective cover enclosing said hand piece comprising:
        a single-piece body substantially conforming in shape and dimensions with said hand piece, said body comprising first and second halves symmetric along a longitudinal axis of said body;
        hinge means forming a part of said single-piece body for rotating said first half of said body for engagement with said second half thereby defining an enclosure adapted to enclose said hand piece; and
        integral means for retaining said first and second halves in engagement and enclosure of said hand piece.

17. The dental appliance of claim 16 wherein said hand piece comprises an air-driven hand piece.

18. The dental appliance of claim 16 wherein said integral means for rotating comprises a strip of plastic adapted to operate as a hinge.

19. The dental appliance of claim 16 wherein said protective cover comprises a layer of substantially rigid plastic.

20. A method of constructing a single piece protective cover for a dental hand piece comprising the steps of:
    constructing a mold having a shape and dimensions corresponding to a selected model of dental hand piece and defining symmetric halves of head, neck and handle portions of the protective cover and hinge means for folding the halves into engagement; and
    forming the single piece cover including the symmetric halves of the head, neck and handle portions and the hinge means from a selected plastic using the mold.

21. The method of claim 20 wherein said step of forming comprises the step of injection molding.

22. The method of claim 20 wherein said step of forming comprises the step of thermo-forming.

23. The method of claim 20 wherein the selected plastic is selected to create a substantially rigid protective cover.

* * * * *